US008764653B2

(12) United States Patent
Kaminska et al.

(10) Patent No.: US 8,764,653 B2
(45) Date of Patent: Jul. 1, 2014

(54) APPARATUS FOR SIGNAL DETECTION, PROCESSING AND COMMUNICATION

(76) Inventors: Bozena Kaminska, Vancouver (CA); Yindar Chuo, Burnaby (CA)

( * ) Notice: Subject to any disclaimer, the term of this patent is extended or adjusted under 35 U.S.C. 154(b) by 1143 days.

(21) Appl. No.: 11/895,040

(22) Filed: Aug. 22, 2007

(65) Prior Publication Data
US 2009/0054742 A1 Feb. 26, 2009

(51) Int. Cl.
*A61B 5/00* (2006.01)
*G06F 19/00* (2011.01)

(52) U.S. Cl.
CPC ........... *G06F 19/30* (2013.01); *A61B 2562/164* (2013.01); *A61B 5/6833* (2013.01)
USPC ...................................................... 600/301

(58) Field of Classification Search
None
See application file for complete search history.

(56) References Cited

U.S. PATENT DOCUMENTS

| 6,603,987 | B2 | 8/2003 | Whitson | |
|---|---|---|---|---|
| 6,652,478 | B1 | 11/2003 | Gartstein | |
| 7,132,054 | B1 | 11/2006 | Kravitz | |
| 7,497,827 | B2 * | 3/2009 | Brister et al. | 600/309 |
| 2003/0181863 | A1 | 9/2003 | Ackley | |
| 2005/0096513 | A1 * | 5/2005 | Ozguz et al. | 600/301 |
| 2005/0131288 | A1 * | 6/2005 | Turner et al. | 600/391 |
| 2006/0020187 | A1 * | 1/2006 | Brister et al. | 600/345 |
| 2007/0066873 | A1 * | 3/2007 | Kamath et al. | 600/300 |
| 2007/0244374 | A1 * | 10/2007 | Vyssotski et al. | 600/301 |
| 2008/0091089 | A1 * | 4/2008 | Guillory et al. | 600/301 |
| 2008/0091090 | A1 * | 4/2008 | Guillory et al. | 600/301 |
| 2008/0091762 | A1 * | 4/2008 | Neuhauser et al. | 709/201 |
| 2008/0132749 | A1 * | 6/2008 | Hegde et al. | 600/16 |
| 2008/0188731 | A1 * | 8/2008 | Brister et al. | 600/345 |
| 2008/0275327 | A1 * | 11/2008 | Faarbaek et al. | 600/382 |
| 2010/0063365 | A1 * | 3/2010 | Pisani et al. | 600/301 |

FOREIGN PATENT DOCUMENTS

WO WO2008/095318 8/2008

OTHER PUBLICATIONS

Xijun, et al. 2005. Design of Sensor Node Platform for Wireless Biomedical Sensor Networks, 27th International Conference of the Engineering in Medicine and Biology Society Sep. 1-4, 2005, Shanghai, China.
Lo, B. et al., 2005. Body Sensor Network—A Wireless Sensor Platform for Pervasive Healthcare Monitoring. Adjunct Proceedings of the 3rd International Conference on Pervasive Computing, Munich, May 8-13, 2005 pp. 77-80.

(Continued)

*Primary Examiner* — Gary Jackson
*Assistant Examiner* — Bobby Soriano
(74) *Attorney, Agent, or Firm* — Hugh McTavish

(57) ABSTRACT

An apparatus for monitoring one or more than one biological parameter is provided. The apparatus comprises two or more than two layers, each layer comprising a flexible substrate, the two or more than two layers comprising two or more than two sensors for sensing the one or more than one biological parameter; a signal conditioning module in communication with one or more than one of the two or more than two sensors; a signal processor in communication with the signal conditioning module and producing a processed signal; a communication module in communication with the signal processor and transmitting the processed signal to a storage module, a display device, a host processing system, or a combination thereof; and a power module to provide power to the two or more than two sensors, the signal conditioning module, the signal processor, and the communication module.

21 Claims, 12 Drawing Sheets

(56) References Cited

OTHER PUBLICATIONS

Lo, B., and Yang, 2005. Architecture for Body Sensor Networks. Workshop paper—Perspective in Pervasive Computing IEEE Savoy Place, 2005, pp. 23-28.

McKay et al., 1999. Sternal acceleration ballistocardiography and arterial pressure wave analysis to determine stroke volume. Clin. Invest Med. 22:4-14.

Wang, L et al., 2002. An Integrated Sensor Microsystem for Industrial and Biomedical Applications. IEEE Instrumentation and Measurement Technology Conference, Anchorage, AK May 21-23, 2002.

Carmichael et al. 2007. Integrated Env and Wear Monit Tech for Med Appl. Festival of International Conferences on Caregiving, Disability, Aging and Technology (FICCDAT) Jun. 16-19, 2007, Toronto Canada.

Purdon P.L. et al. 2001. Ballistocardiogram Removal and Motion Correction for EEG in the Magnet. Proc. Intl. Soc. Mag Reson Med. 9: 29 (2001).

Mathews DJ and Gaynor, MP. 2003. Amkor Technology Inc. RF System in Package: Tradeoffs Govern the Cost, Size and Performance Equation. Chip Scale Review, Jul. 2003.

Mathews DJ and Gaynor, MP. 2003. Amkor Technology Inc. RF System in Package: Considerations,. Technologies and Solutions. Chip Scale Review, Jul. 2003.

* cited by examiner

APPARATUS FOR SIGNAL DETECTION, PROCESSING AND COMMUNICATION

FIELD OF INVENTION

The present invention relates to the field of medical devices.

BACKGROUND OF THE INVENTION

Measurement of biological parameters such as an electrocardiogram (ECG) is a well-known and important aspect of medical monitoring systems. Advances in the sensors, microelectronics and data storage and processing have made possible the miniaturization of medical monitoring equipment such as ECG, such that a subject may wear the sensors for an extended period outside of a hospital environment.

Rarely however, is a biological parameter monitored in isolation. Several parameters may be monitored intermittently or over time to provide information on a subject's physical condition or health.

Xijun et al 2005 ($27^{th}$ International Conference of the Engineering in Medicine and Biology Society Sep. 1-4, 2005) describe a lightweight, low power sensor that may be used as an electrocardiogram sensor.

Lo et al 2005 ($3^{rd}$ International Conference on Pervasive Computing, Munich, May 8-13, 2005. pp 77-80) describe a network of sensors to monitor various biological parameters.

Lo and Yang 2005 (The Perspective in Pervasive Computing IEE Savoy Place, 2005 pp 23-28) describe a node for a sensor network that may be used on a subject, to facilitate the use of wireless sensors.

SUMMARY OF THE INVENTION

The present invention relates to an apparatus for signal detection, processing and communication It is an object of the invention to provide an improved method for the simultaneous detection of multiple biological parameters. According to one aspect of the invention, there is provided an apparatus for monitoring one or more than one biological parameter, the apparatus comprising two or more than two layers, each layer comprising a flexible substrate, the two or more than two layers comprising two or more than two sensors for sensing the one or more than one biological parameter; a signal conditioning module in communication with one or more than one of the two or more than two sensors; a signal processor in communication with the signal conditioning module and producing a processed signal; a communication module in communication with the signal processor and transmitting the processed signal to a storage module, a display device, a host processing system, or a combination thereof; a power module to provide power to the two or more than two sensors, the signal conditioning module, the signal processor, and the communication module.

According to another aspect of the invention, there is provided an apparatus for monitoring one or more than one biological parameter, the apparatus comprising a first layer comprising a flexible substrate and having disposed thereon a first and a second sensor, a second layer comprising a flexible substrate and having disposed thereon a signal processor, a communication module in communication with the signal processor; wherein the first and the second sensors independently relay a signal to the signal processor, and the signal processor relays a processed signal to the communication module for transmission of the processed signal to a storage module, a display device or a host processing system.

According to another aspect of the invention, there is provided a method for monitoring one or more than one biological parameter, the method comprising (i) positioning an apparatus for monitoring at least one biological parameter, on a subject, the apparatus comprising two or more than two layers, each layer comprising a flexible substrate, the layers comprising: two or more than two sensors for sensing the one or more than one biological parameter; a signal conditioning module in communication with one or more than one of the two or more than two sensors; a signal processor in communication with the signal conditioning module and producing a processed signal; a communication module in communication with the signal processor and transmitting the processed signal to a storage module, a display device, a host processing system, or a combination thereof; a power module to provide power to the two or more than two sensors, the signal conditioning module, the signal processor, and the communication module; (ii) thereby monitoring the processed signal for an alteration in a biological parameter.

In accordance with another aspect of the invention, a signal conditioning module may be included in the apparatus, and may comprise part of the signal processor.

In accordance with other aspects of the invention, an adhesive layer may also be provided. The adhesive may be a acoustic, thermal, chemical, fluid or electrical insulator. The adhesive may be optically clear, or may act as a filter for specific wavelengths, or ranges of wavelengths, of light. In some embodiments the adhesive layer may be electrically conductive.

In accordance with other aspects of the invention, the apparatus may further comprise an adhesive layer.

In accordance with other aspects of the invention, the adhesive layer may incorporate a dermal penetrating device, the device being in communication with the subject's tissue and with a sensor in a first layer of the apparatus.

In accordance with other aspects of the invention, the biological parameters may be independently selected from the group comprising movement, heart rate, temperature, biopotential, respiration, skin moisture, skin conductivity, hemoglobin oxygen saturation, sound, light absorption or reflection, glucose level, protein level, amino acid level, lipid level, fatty acid level or combination thereof. Levels of glucose, protein, amino acid, lipid, fatty acid or combinations thereof may be measured in the in blood, dermal layers/skin, intracellular fluid, extracellular fluid, interstitial space, extracellular compartment, lymphatic fluid, muscle layers, muscle tissue, combinations thereof.

In accordance with other aspects of the invention, the power module may comprise a battery, and/or a power regulator. The power module may alternately be a piezoelectric crystal, a radiofrequency power source, a thermocouple, or an electroactive polymer.

In accordance with another aspect of the invention, the two or more than two sensors are independently selected from the group comprising accelerometer, electrode, thermometer, thermal diode, galvanometer, LED, photodiode, microphone, vibration sensor, optical diode, glucometer, spectrometer, pH meter, spectrophotometer, or a combination thereof.

In accordance with another aspect of the invention, one of the two or more than two sensors may be an accelerometer.

In accordance with another aspect of the invention, one of the two or more than two sensors may be an optical sensor.

In accordance with another aspect of the invention, one of the two or more than two sensors may be a spectrometer.

In accordance with another aspect of the invention, one of the two or more than two sensors may comprise an electrode for monitoring biopotential.

In accordance with another aspect of the invention, one of the two or more than two sensors may be an acoustic sensor.

In accordance with another aspect of the invention, a first sensor may be an accelerometer and a second sensor may comprise electrodes for monitoring biopotential.

In accordance with another aspect of the invention, a first sensor may be an accelerometer and a second sensor may be an optical sensor.

In accordance with another aspect of the invention, a first sensor may be an acoustic sensor and a second sensor may comprise electrodes for monitoring biopotential.

In accordance with another aspect of the invention, a first sensor may be an optical sensor and a second sensor may comprise electrodes for monitoring biopotential.

In accordance with other aspects of the invention, the flexible substrate may be polyimide. In other aspects, the apparatus may be partially or fully encapsulated with an elastomeric polymer.

This summary of the invention does not necessarily describe all features of the invention. Other aspects and features of the present invention will become apparent to those of ordinary skill in the art upon review of the following description of specific embodiments of the invention.

BRIEF DESCRIPTION OF THE DRAWINGS

These and other features of the invention will become more apparent from the following description in which reference is made to the appended drawings wherein.

DETAILED DESCRIPTION

Figure 1:
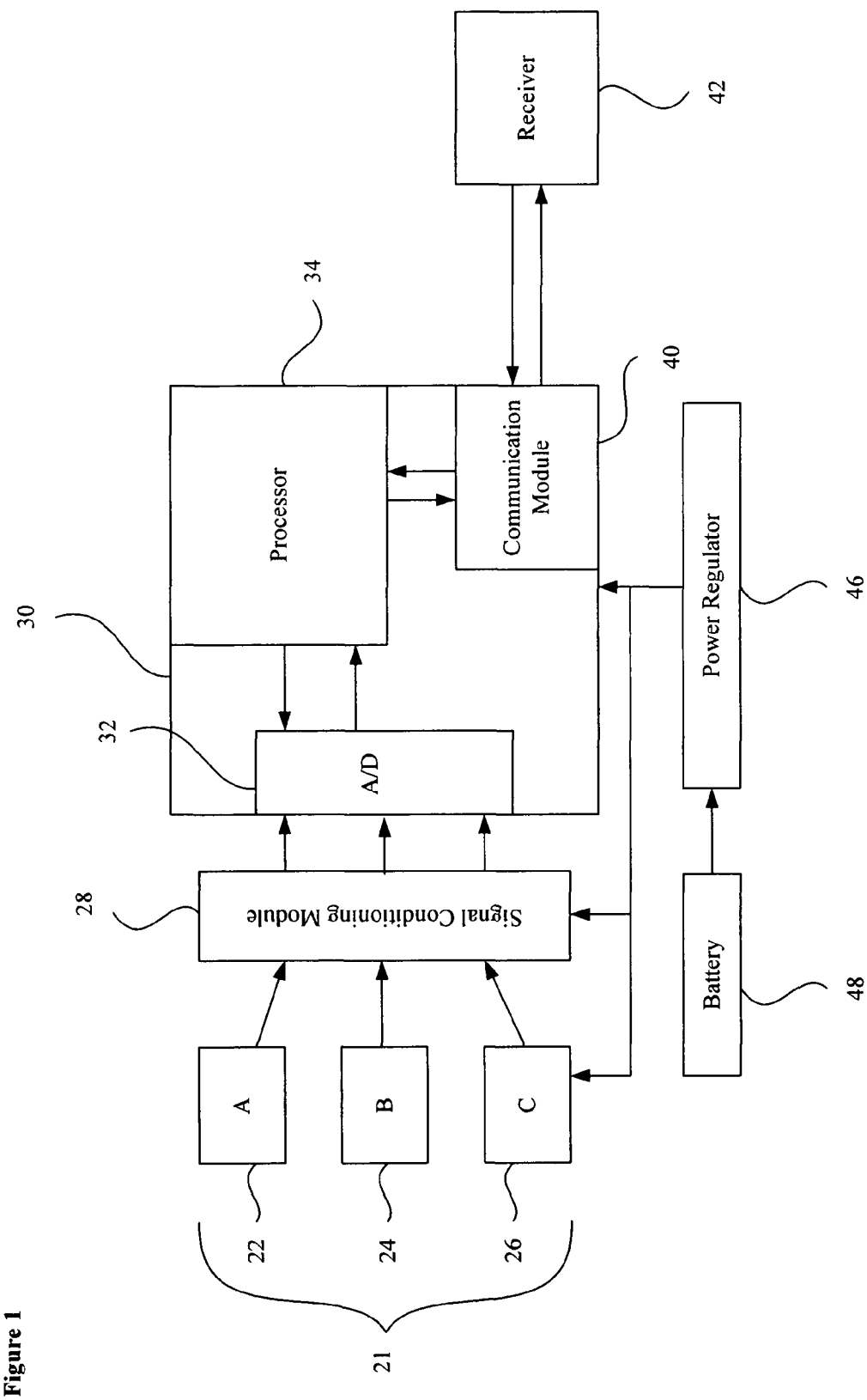
FIG. 1 shows an illustrative layout of components of a system comprising an apparatus in accordance with an embodiment of the invention.

The present invention provides an apparatus for monitoring one or more than one biological parameter, the apparatus comprising a sensor for detecting the one or more than one biological parameter, a signal processor and a communication module.

For example, one aspect of the invention provides an apparatus for monitoring one or more than one biological parameter, the apparatus comprising two or more than two layers, each layer comprising a flexible substrate, the two or more than two layers comprising two or more than two sensors for sensing the one or more than one biological parameter; a signal conditioning module in communication with one or more than one of the two or more than two sensors; a signal processor in communication with the signal conditioning module and producing a processed signal; a communication module in communication with the signal processor and transmitting the processed signal to a storage module, a display device, a host processing system, or a combination thereof, a power module to provide power to the two or more than two sensors, the signal conditioning module, the signal processor, and the communication module. One or more layers of the multilayered apparatus may comprise one or more than one sensor. The layers of the multilayered apparatus may be arranged in any order as desired, and each layer of the multilayered apparatus may comprise a different assortment of the components. The multilayered apparatus may also comprise additional layers, for example but not limited to one or more than one adhesive layer, one or more than one insulating layer, or a combination thereof.

For example, one aspect of the present invention provides an apparatus for monitoring one or more than one biological parameter, the apparatus may comprise one or more than one flexible substrate arranged as layers, where each of the layers within the multilayered apparatus comprise components to facilitate sensing of one or more than one biological parameter to produce a signal, processing the signal, and optionally, communicating the signal to a host processor. One or more layers of the multilayered apparatus may comprise one or more than one sensor, a second layer may comprise a signal processor, and optionally a communication module in communication with the signal processor or a third layer may comprise the communication module in communication with the signal processor. For example the apparatus may comprise two or more than two sensors. The layers of the multilayered apparatus may be arranged in any order as desired, and each layer of the multilayered apparatus may comprise a different assortment of the components. The multilayered apparatus may also comprise additional layers, for example but not limited to one or more than one adhesive layer, one or more than one insulating layer, or a combination thereof. The present invention further provides methods for monitoring one or more than one biological parameter. For example, the method may comprise (i) positioning an apparatus for monitoring at least one biological parameter, on a subject, the apparatus comprising two or more than two layers, each layer comprising a flexible substrate, the layers comprising: two or more than two sensors for sensing the one or more than one biological parameter; a signal conditioning module in communication with one or more than one of the two or more than two sensors; a signal processor in communication with the signal conditioning module and producing a processed signal; a communication module in communication with the signal processor and transmitting the processed signal to a storage module, a display device, a host processing system, or a combination thereof; a power module to provide power to the two or more than two sensors, the signal conditioning module, the signal processor, and the communication module; (ii) thereby monitoring the processed signal for an alteration in a biological parameter. Measuring or monitoring one or more than one biological parameters at a single locus Referring to FIG. 1, which is not to be considered limiting in any manner, a schematic block diagram of an apparatus according to some embodiments of the invention is shown. The apparatus may be generally described as comprising a sensor array 21, a signal conditioning module, a microcontroller and a communication module. Optionally, a power module such as a battery, may be included. The sensor array may comprise at two or more than two sensors. A non-limiting example of a sensor array comprising three sensors, sensor A 22, sensor B 24 and sensor C 26 is shown. The sensors generate data about various physiological conditions or other biological parameters of the subject (described below) and convert the signal to an electrical output. Each electrical signal may be conveyed from the sensor to a signal conditioning module 28, where the electrical signal may be conditioned by a filter, amplifier or other conditioning method as would be know to one of skill in the art. Each conditioned signal may then be conveyed to a microcontroller 30, where the conditioned signal may be digitized and processed. Optionally, if the signal received by the microcontroller 30 is an analog signal, it may be converted to a digital format, for example by an A/D (analogue/digital) converter 32, and the resulting digital signal processed. A processed signal may be alternately referred to as, for example, 'data'. The data may be communicated via a communication module 40 to a receiver 42 connected to a recording device (not shown), a storage device (not shown), a second processor (not shown), or other host processing system as would be known in the art, for further analysis. Alternately, the receiver 42 may be in communication with the processor 34, and the data transmitted for further processing by way of a wired connection with a recording device (not shown), a storage device (not shown), a second processor (not shown), or other host processing system as would be known in the art. A power module comprising for example, a regulator 46 and a battery 48, may be used to provide and regulate the power needs of the apparatus. Alternate power sources may also be used. A microcontroller may include a microprocessor, as well as other elements, such as those described herein.

Components or modules of the apparatus according to some embodiments of the invention are in communication with, convey signals, or both are in communication with and convey signals, to or from other components or modules using conventional communication components, for example a conductive wire, fiber optics, or other communication element, as is known in the art. Alternately, a signal may be conveyed by wireless methods such as a radio frequency. Components of the apparatus may also convey signals to or from external devices, for example a computer, a host processing system, a display device such as a computer monitor or a computer storage device or recording device, as are known in the art. Again, the signals may be conveyed in a conventional manner using communication elements or wireless methods as are known in the art, and exemplified herein.

A power module may include, for example, a battery, and optionally a power regulator. In other embodiments, a power module may be a piezoelectric crystal, a radiofrequency power source, a thermocouple, an electroactive polymer, or the like, as are known in the art.

FIG. 1 illustrates the interaction of the various components of a sensor as laid out in a single plane for ease of illustration. Apparatus according to various embodiments of the invention may comprise a plurality of layers, with the various components including sensors, signal processing, signal communication, and power source distributed over the layers. The choice of layer for positioning a particular component may be dependent on the role of the component, need for contact with the subject's skin or tissue, need for insulation, or for ease of access. Additionally, one or more than one intervening layer may be provided to insulate one component from another. The one or more than one intervening layer may provide, for example, thermal, electrical, or acoustic insulation. The one or more than one intervening layer (s) may further provide one or more than one communication element that ensures communication from one component to another that may be located on the same, or different, layers.

Figure 2:
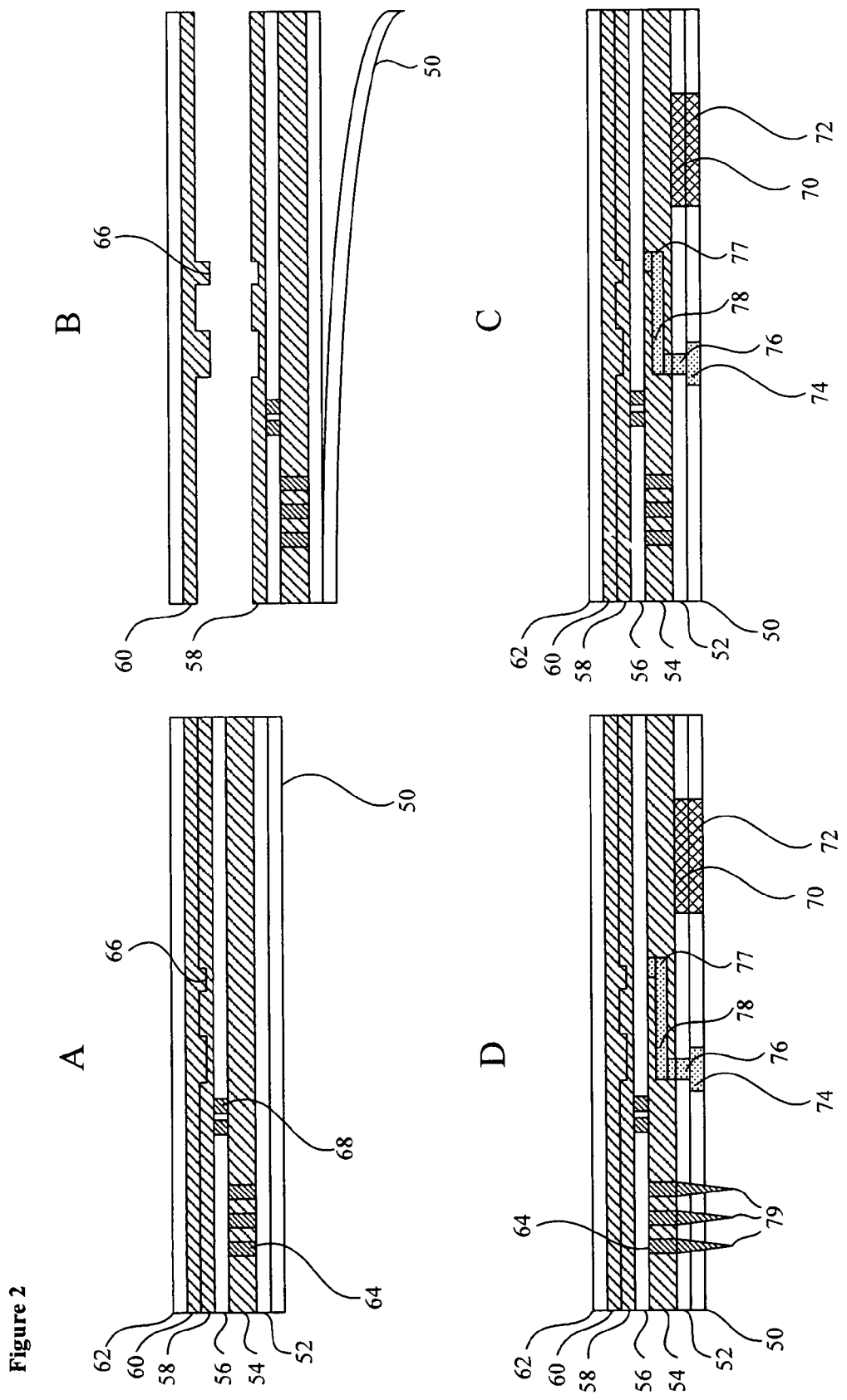
FIG. 2 shows a sectional view of one embodiment of the invention, illustrating layers and connections between the layers.

FIG. 2A shows a sectional view of an example of an apparatus of the present invention comprising three layers, two intervening layers, and an adhesive layer. For ease of display, no sensors, receivers, microcontroller and the like or are shown. A double-sided adhesive layer 50, contacts a subject's skin and a first layer 52. The first layer 52 is separated from a second layer 56 by a first intervening layer 54. The first layer and second layer are in communication in the example illustrated by one or more than one first communication element 64, that passed through the first intervening layer 54. The second layer 56 is separated from a third layer 60 by a second intervening layer 58. One or more than one second communication element 68, provides for communication between the first intervening layer 54 and a sensor (not shown) located on the second intervening layer 58. The first communication element 64, second communication element 68 or both the first and the second communication elements (64, 68) may be an electrical connection, a fiber optic connection, or a microfluidic connection. A third intervening layer 60 adjacent to the second intervening layer 58 may be reversibly or permanently connected to the second intervening layer 58 by way of fitting 66. FIG. 2B shows releasable attachment of the third layer 62 from one or more than one layer of the apparatus. The fitting 66 may comprise one or more than one interlocking ridge and valley on the contacting surfaces of the layers to be connected, or other interlocking or inter-fitting structures. Alternately, the join may comprise a permanent or reversible adhesive. The adhesive layer 50 may also independently detachable from the majority of the layers of the apparatus. In this way, the apparatus may be reused by reattaching a new adhesive layer 50.

It is to be understood that the use of adhesive layer 50 is optional and may not be required depending upon the application. For example, first layer 52 may comprise adhesive elements disposed along the periphery of the layer.

An alternate embodiment of the apparatus is shown in FIG. 2C. The like elements are indicated using the same numerical identifiers as in FIGS. 2A and 2B. For ease of display, not all components, for example, sensors, receivers, microcontroller and the like are shown. The apparatus shown in FIG. 2C further comprises a third communication element (72), for example a window or fiber optic, in the adhesive layer 50, with a corresponding sensor 70 in the first layer 52. The window or fiber optic (third communication element) 72 may provide optical access to a subject's skin surface, for example, to accommodate an optical sensor, or other sensor having light transmitting, receiving, or both light transmitting and receiving, capabilities. Non-limiting examples of such sensors are described generally in Table 1 and herein.

Also shown in FIG. 2C is a forth communication element 74 in the adhesive layer 50, that is aligned with corresponding, fifth and sixth communication elements 76 and 77 in the first layer 52. Communication elements 76, 77 and 78 combine to provide communication between the adhesive layer (50) and a sensor (not shown) located on the second layer 56. The communication elements 74, 76, 77, 78 may be configured to permit, for example, fluidic communication, optic communication, or electric communication between the subject's skin surface or tissue and one or more than one sensor located on the first 52, second 56, or both the first and second (52, 56), layers of the apparatus. One or more than one of the communication elements 74, 76, 78 are in operational contact with one or more than one sensor, so that the fluidic sample, or optic or electric signal is received by the sensor for processing.

It will be apparent to those skilled in the relevant art that additional layers may be found in other embodiments, and would be assembled and function in an analogous manner.

The adhesive layer (50) facilitates the removable attachment of the apparatus to the site of use. The adhesive layer may be double-sided, and may be of any conventional material suitable for the intended use — for example, if the sensor is used on the skin or tissue of a subject, the adhesive may be a double-sided medical adhesive. Alternately, the adhesive may have other properties, for example, the adhesive may have acoustic, thermal, chemical, fluid or electrical insulating properties. The adhesive may be optically clear, or may filter selective wavelengths of light. In another embodiment, the adhesive may be conductive, for example, to facilitate measurement of skin conductivity, or to permit transmission of a biopotential from the subject's skin or tissue surface to a sensor comprising an electrode. In some embodiments, the adhesive may allow diffusion of fluid, salts, analytes, proteins or other molecules or compounds from the surface to the sensor. The adhesive layer (50) may allow for selective diffusion, for example, hydrophobic compounds or molecules may be prevented from diffusing by a diffusible adhesive having a hydrophilic composition. In some embodiments, the adhesive may have regions with different properties, for example, the adhesive over the majority of the surface may be electrically insulating, with specific regions aligned with an electrode, or an electrically conductive material.

In another embodiment, the adhesive layer may incorporate a dermal penetrating device, such as a micro-needle (79; see FIG. 2D). Micro-needles and methods of fabrication are described in, for example U.S. Pat. Nos. 6,603,987, 7,132, 054, 6,652,478 or US Patent Application 2003/0181863, all of which are herein incorporated by reference. Choice of a particular type, material or method of fabrication of the micro-needle may vary with the intended use or sensor with which the micro-needles communicate, and is within the ability of one skilled in the relevant art. Micro-needles may penetrate the outer dermal layer and provide fluidic contact with the capillary or intercellular environment, which may be sampled continually or intermittently by one or more than one sensor of the apparatus as described herein, and thus providing information on proteins, blood or tissue chemistry, analytes etc. In this example, one or more than one micro-needle (79) may be in fluidic communication with a sub-dermal skin layer and sample, blood, cells or other tissues, and communicate the sample through one or more than one communication elements (for example 64, 74, 76, 77, 78) of the apparatus to a desired sensor. In this way, the micro-needles may convey one or more than one sample to a sensor within the apparatus for further analysis.

A wide variety of properties, including biological parameters, biopotentials, physical measurements, optical properties, and chemical and analyte profiles may be measured, recorded, observed, or detected by one or more than one sensor, or sensor array, according to some embodiments of the invention. The measuring, recording, observing or detecting may be generally described as 'monitoring'. Examples of these biological parameters may include, but are not limited to, those listed in Table 1. Biological parameters such as glucose levels, protein levels, amino acid levels, lipid levels, fatty acid levels or the like may be measured in blood, dermal layers/skin, intracellular fluid, extracellular fluid, interstitial space, extracellular compartment, lymphatic fluid, muscle layers, muscle tissue, combinations thereof, or the like. Examples of sensor types or devices that may be suitable for measuring or detecting these biological parameters are also shown in Table 1. Sensors may be independently selected from the group comprising an accelerometer, electrode, thermometer, thermal diode, galvanometer, LED, photodiode, microphone, vibration sensor, optical diode, glucometer, spectrometer, pH meter, spectrophotometer, combinations thereof, or the like. Other biological properties or parameters and relevant sensor types or detection methods or devices and how to use and interpret the resulting data or signals will be known to those skilled in the relevant art. Depending on the nature of the signal, the form in which is it received, analyzed or used, it may be referred to as 'data', a 'reading', 'information' or the like.

TABLE 1

| Property or Parameter | Examples of Sensor type, device or technique |
|---|---|
| Movement or motion | Accelerometer, 3-axis MEMS accelerometer (eg. ST Microelectronics, Analog Devices, Kionix, Freescale) |
| Heart rate | Electrocardiogram |
| Temperature | Thermometer, thermal diode, MEMS thermal sensor |
| Galvanic skin response | Galvanometer |
| Biopotential | electrodes |
| Hemoglobin oxygen saturation | Infrared light absorption/near infra-red spectrometry/pulse oximetry |
| Respiration rate or depth | Microphone, accelerometer, vibration sensor, (alone or in combination) |
| Sound | Microphone |
| Light absorption of tissue | Optical diode/photodiode |
| Light retransmission of tissue | Optical diode/photodiode |
| glucose | Glucometer |
| Protein or amino acid | Spectrometry, other chemical detection methods |
| Lipid or fatty acid | Spectrometry, other chemical detection methods |
| Analytes in tissue or on skin | Spectrometry, other chemical detection methods |

In some embodiments, the apparatus may comprise a plurality of the same general type of device or sensor type. For example, simultaneous measurement of diaphragm movement (ie from respiration), tilt of the body and ballistocardiography may involve three separate accelerometers, each of which may be designed to measure a particular direction or magnitude of motion.

Examples of signal conditioning methods that may be applied to the electrical signal, according to some embodiments of the invention may include, but are not limited to, filtering, amplification or noise reduction. For example, a Fast Fourier transform or a wavelet transform may be used to reduce or remove background noise from the signal. Selection of filter methods is dependent on the signal, and the sensor used to generate it, and will be within the ability of one skilled in the relevant art. Without wishing to be bound by theory, signal conditioning at the point of data collection may result in reduced signal noise and improved signal quality.

Figure 11:
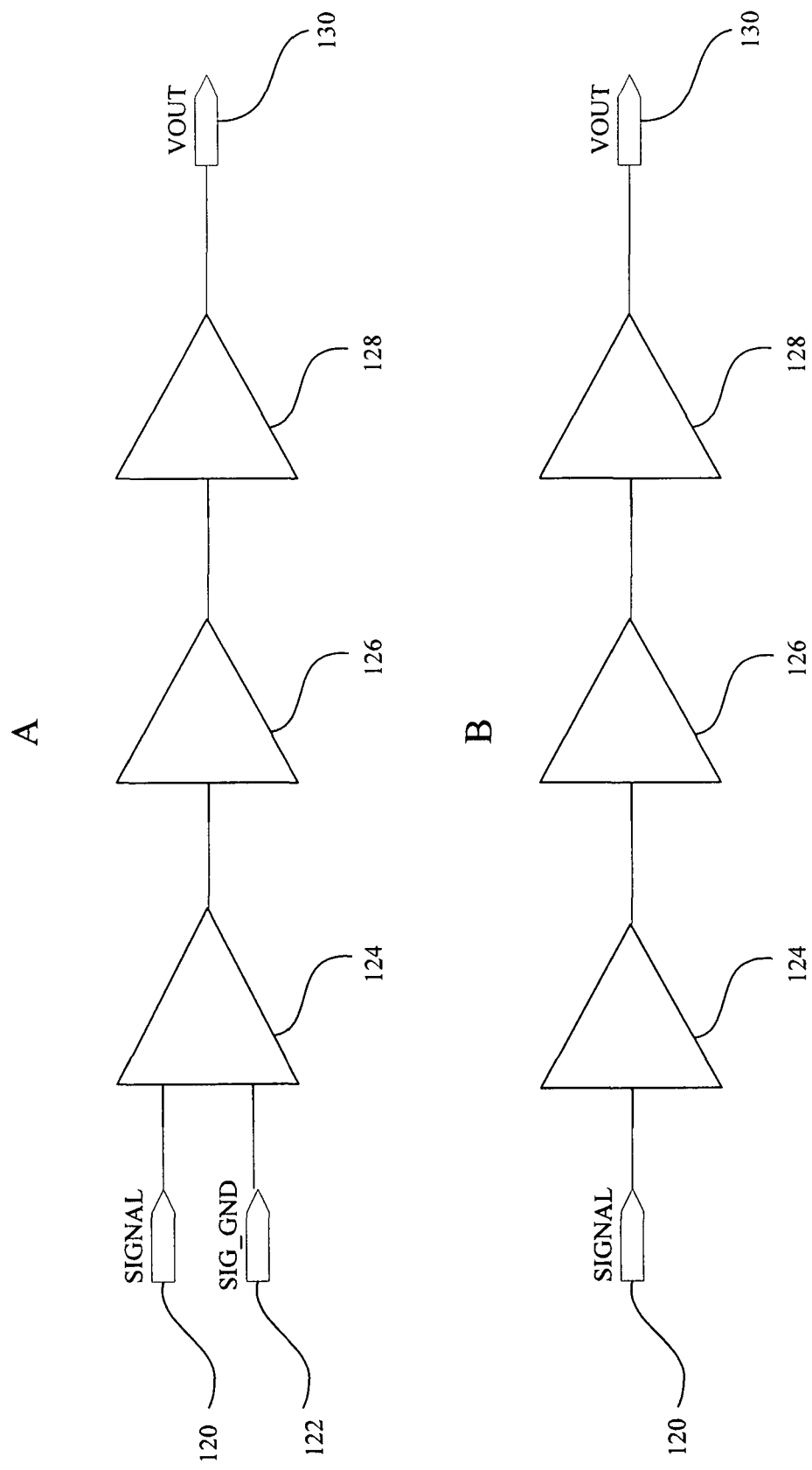
FIG. 11 shows a signal conditioning scheme for a differential input (A) or a single input (B), in accordance with an embodiment of the invention.

A non-limiting, example illustrating a general signal conditioning scheme, as is known in the art is shown in FIG. 11A. A differential signal input comprising signal input 120 and signal input ground 122, or alternately, any two or more signals from any two or more sensors of the apparatus, may be provided to a first amplifier group 124. Amplifier group 124 may be, for example, a high-performance instrumentation amplifier (comprising, for example a high slew-rate, fast response, large gain-bandwidth-product, rail-to-rail input and output), or a configuration of high-performance operational-amplifiers to form a differential input stage. This input stage may provide high input-impedance to maintain signal quality, and sets an initial (large) gain for small-biosignals. A second amplifier group 126 provides a filtering function, for example, low-pass filtering, band-pass filtering, or high-pass filtering. A plurality of frequency bands, for example, frequencies $\alpha$ (alpha) to $\beta$ (beta), and frequencies $\phi$ (theta) to $\omega$ (omega) may be selected in the amplifier group 126. A third amplifier group 128 provides a final amplification and, in some embodiments, additional noise removal to provide a conditioned signal suitable for digitization and processing. The signal output 130 of the signal conditioning module is then ready for further processing. FIG. 11B shows an alternate embodiment, where a single signal input 120 is provided to a first amplifier group. Amplifier groups 124, 126, 128 are as described.

The microcontroller may comprise a mixed signal microprocessor for digitizing, recording and storage of the signal, according to some embodiments. Microcontrollers comprising a mixed signal microprocessor are available from various suppliers and manufacturers; alternately they may be manufactured to suite a particular application, according to know methods and procedures. Examples of mixed signal processors available commercially include, but are not limited to, TI RF and Microcontroller (System on Chip Models CC1010, 1110,2510, 2430), Toumaz Sensium RF microcontroler and Microcontroller SoC, and the like. Additionally, the microcontroller may comprise an integrated transceiver, and/or an integrated data storage device. In some embodiments, the signal conditioning unit may be integrated with the microcontroller.

The communication module may be, as described above, integrated within a microcontroller. Data and signals may be conveyed by wireless methods such as a radio communication system, or by wired methods such as conventional circuitry using fiber optics, cables, or wires.

Figure 3:
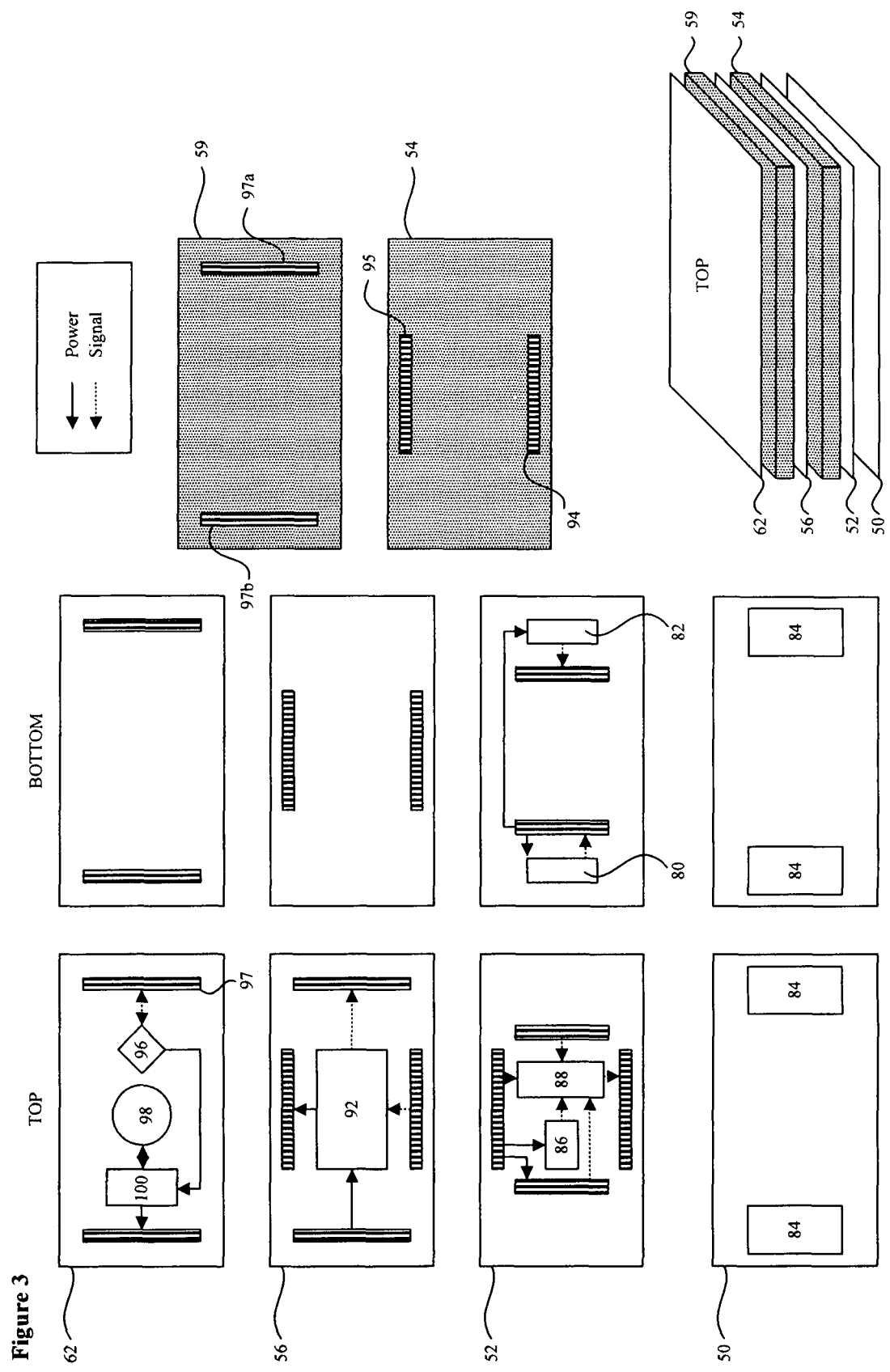
FIG. 3 shows an exploded view of an apparatus according to one embodiment of the invention, comprising an optical sensor and accelerometer
Figure 4:
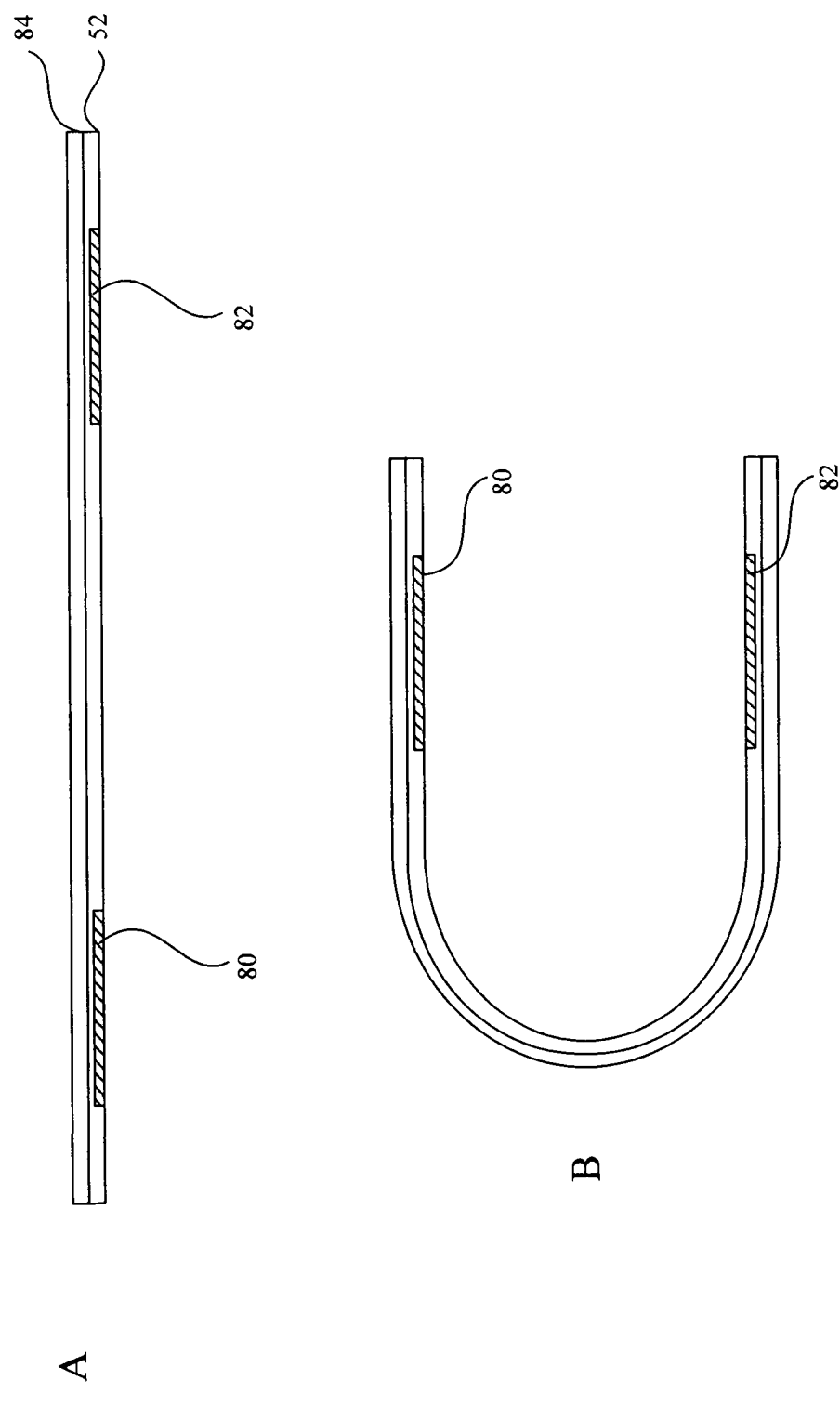
FIG. 4 shows a side view of an apparatus according to one embodiment of the invention, comprising an optical sensor configured for use on a subject.

FIG. 3 shows an exploded diagram of a non-limiting example of an apparatus, in accordance with an embodiment of the invention, combining optical sensors for pulse oximetry and an accelerometer in a single apparatus. Each of the first, second and third layers have a first ("top") and second ("bottom") side, and are configured to communicate with the adhesive layer, the intervening layer, or both the adhesive and the intervening layer, on either the first or second side of the layer, to allow integration of the multiple sensors and components of the apparatus. The adhesive layer 50 has two apertures 84 to allow optical communication of the optical sensor modules (LED 82 and photodiode 80) on the bottom of the first layer with the subject's skin surface. As illustrated in FIG. 4, when wrapped around a sample, for example a subject's finger (not shown), the LED (82) and photodiode (80) are opposite each other to permit the absorption of the red light to be measured and thus the blood oxygen saturation determined, according to known methods. A communication element 90 relays a signal from the optical sensor modules (82 and 80) to the signal conditioning module 88. An accelerometer 86 on a top side of the first layer 52 also may communicate a signal to the signal conditioning module 88, to provide positional data. The signal conditioning module 88 is in communication with a microcontroller 92 on a top side of the second layer 56 by way of communication elements 94, 95 in the intervening layer 54. The microcontroller 92 digitizes and processes the signals, which may be communicated to a recording device, a storage device, a host processing system, or other device, or the like, as are known in the art. The apparatus may further comprise a transceiver (not shown) functionality for sending and receiving data, signals, or data and signals, from other sensors or external equipment such as a computer or host processing device. The microcontroller 92 is in communication with an antenna 96 on a top side of the third layer 62 by way of communication element 97a, 97b in the second intervening layer (layers 58/60, represented here as a single layer 59 for simplicity of illustration). A battery 98, disposed on the top side of the third layer 62, provides power to the sensors, microcontroller 92, antenna 96 and transceiver (not shown). Optionally, the apparatus may include a power converter 100 that may receive power harnessed from radio waves (relayed by the antenna 96) to provide meet the power needs of the sensors, microcontroller, antenna and transceiver. Additionally, if the battery 98 is a rechargeable battery, the power converter 100 may continually recharge the battery.

It will be apparent from the illustrations in FIG. 3 that the intervening layers 54 and 59 are shaped so as to match the contours of the apparatus layers housing the sensors, signal processors, power supply and the like, and to accommodate the various communication elements. For example, the first intervening layer 54 is shaped to fit the contour of a top side of the first layer 52 and a bottom side of the second layer 54 and provides two communication elements 94, 95 disposed to allow communication between the first layer 52 and the second layer 56. Similarly, the second intervening layer 59 is shaped to fit the contour of a top side of the second layer 56 and a bottom side of the top layer 62, and provides two communication elements 97a, 97b disposed to allow communication between the second layer 56 and the third layer 62.

FIG. 4 shows an alternate embodiment of the invention. A sensor comprising a photodiode 80 and a light emitting diode (LED) 82 suitable for pulse oximetry are located in the first layer 52 of the apparatus. For simplicity in illustration, the multiple layers and other components of the apparatus are represented by layer 82. The adhesive layer 50 is also omitted for simplicity in illustration. An apparatus such as this may be wrapped around a subject's finger to provide both blood oxygen saturation data in combination with data obtained from another sensor, such as an accelerometer, to provide positional data simultaneously and synchronously with blood oxygen saturation.

Figure 5:
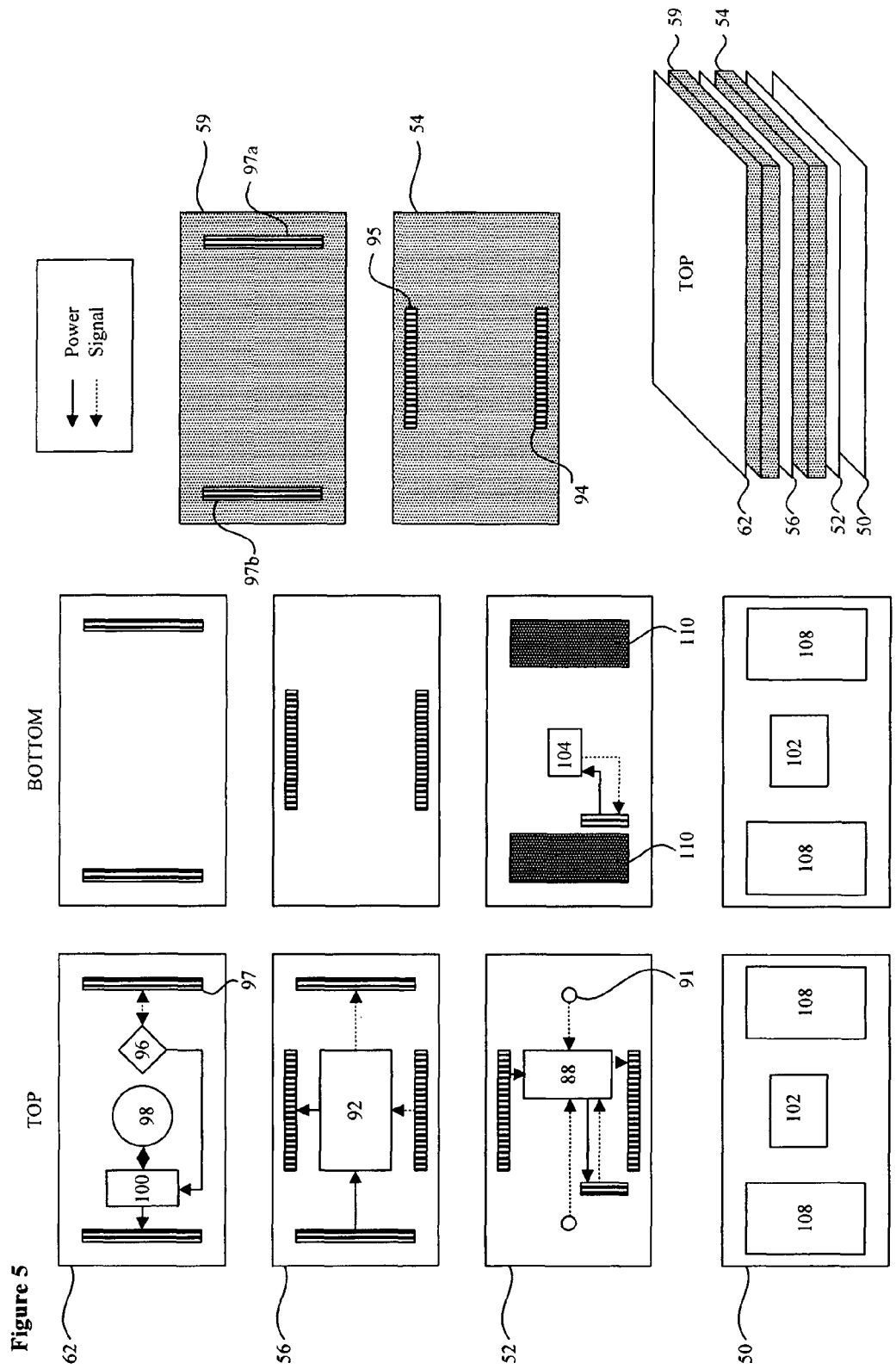
FIG. 5 shows an exploded view of an apparatus according to one embodiment of the invention, comprising an acoustic sensor and a biopotential sensor.

FIG. 5 shows an exploded view of an alternate embodiment of the invention combining acoustic and biopotential sensors in a single apparatus. Similar to the apparatus illustrated in FIG. 3, each of the first, second and third layers have a first ("top") and second ("bottom") side, and are configured to communicate with the adhesive layer, intervening layer, or both layers, on either side, to allow integration of the multiple sensors and components of the apparatus. The adhesive layer 50 has regions of conductivity 108 to allow electrical communication of a sensor 110 on the bottom of the first layer with the subject's skin surface. The sensor 110 may comprise an electrode. The sensor 110 is in communication with the signal conditioning module 88 on the top side of the layer 52 by way of communication element 91. An acoustic sensor 104 on a top side of the first layer 52 relays a signal to a signal conditioning module 88, for example using microcircuitry or fiber optics or the like (not shown), to provide acoustic data. A sensor window 102 in the adhesive layer 50 is aligned with the acoustic sensor 106, providing an uninterrupted access to the subject's skin or tissue. The signal conditioning module 88 is in communication with a microcontroller 92 on a top side of the second layer 56 by way of a communication element 94, 95 in the intervening layer 54. The microcontroller 92 digitizes and processes the signals, which may be communicated to a recording device, a storage device, or a host processing system, or the like, as are known in the art. The apparatus may further comprise a transceiver functionality for sending and receiving data, signals or both data and signals from other sensors or external equipment such as a computer. In a manner similar to that illustrated in FIG. 3 and described in the accompanying text, the microcontroller 92 is in communication with an antenna 96 on a top side of the third layer 62 by way of communication element 97a, 97b in the second intervening layer (layers 58/60, represented here as a single layer 59 for simplicity of illustration). A battery 98 disposed on the top side of the third layer 62 provides power to the sensors, microcontroller, antenna and transceiver. Optionally, the apparatus may include a power converter 100 that may receive power harnessed from radio waves (relayed by the antenna 96) to provide meet the power needs of the sensors, microcontroller, antenna and transceiver. Additionally, if the battery 98 is a rechargeable battery, the power converter 100 may continually recharge the battery.

Figure 6:
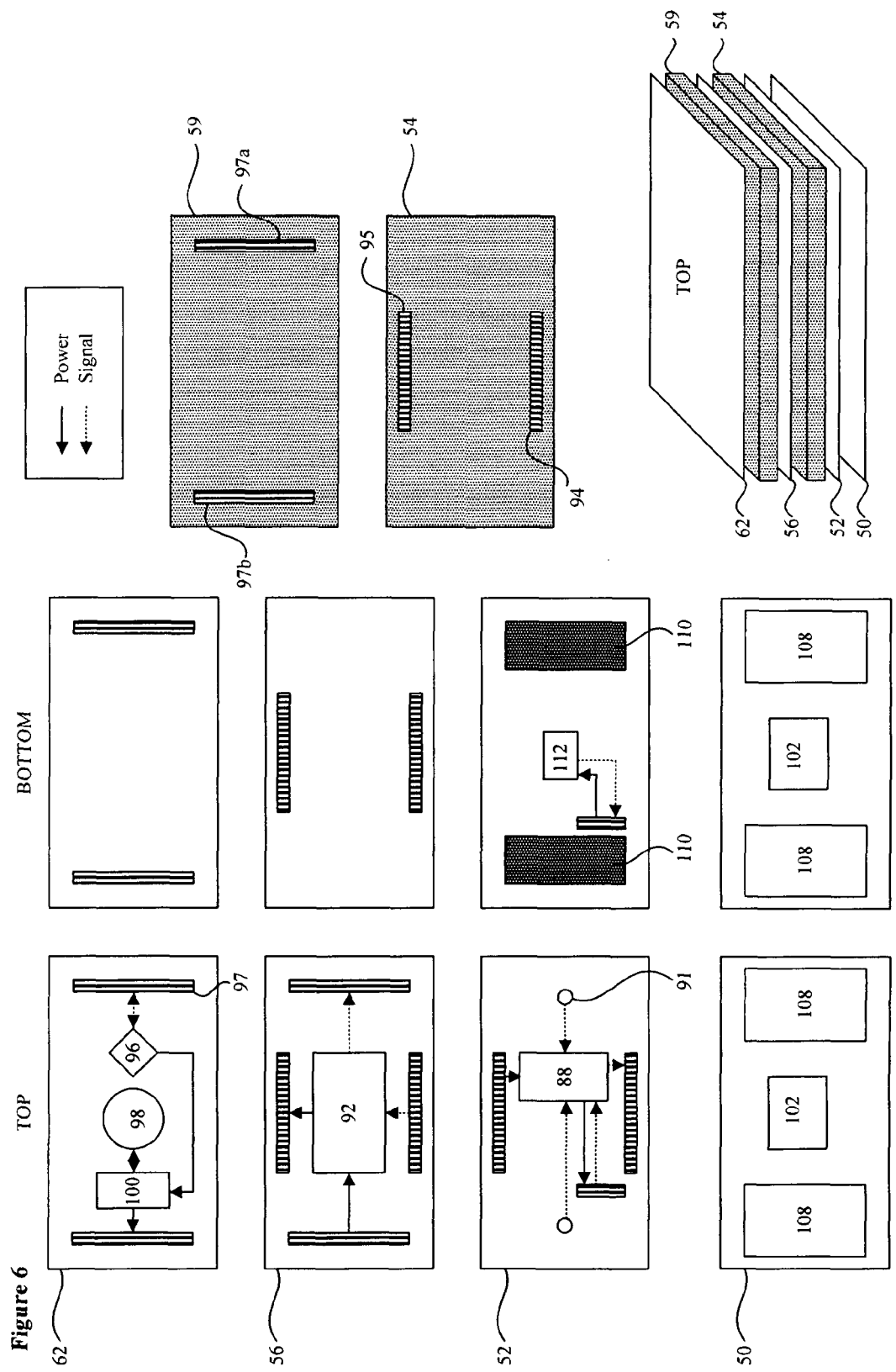
FIG. 6 shows an exploded view of an apparatus according to one embodiment of the invention, comprising an optical sensor and biopotential sensor.

FIG. 6 shows an exploded view of an alternate embodiment of the invention combining optical and biopotential sensors in a single apparatus. Similar to the apparatus illustrated in FIGS. 3 and 5, each of the first, second and third layers have a first ("top") and second ("bottom") side, and are configured to communicate with the adhesive layer, intervening layer, or both layers, on either side, to allow integration of the multiple sensors and components of the apparatus. The adhesive layer 50 has regions of conductivity 108 to allow electrical communication of a sensor 110 on the bottom of the first layer with the subject's skin surface. The sensor 110 may comprise an electrode. The sensor 110 is in communication with the signal conditioning module 88 on the top side of the layer 52 by way of communication element 91. An optical sensor 112 on a top side of the first layer 52 relays a signal to a signal conditioning module 88 using conventional microcircuitry (not shown), to provide optical data. A sensor window 102 in the adhesive layer 50 is aligned with the optical sensor 112, providing an uninterrupted access to the subject's skin or tissue. The signal conditioning module 88 is in communication with a microcontroller 92 on a top side of the second layer 56 by way of a communication element 94 in the intervening layer 54. The microcontroller 92 digitizes and processes the signals, which may be communicated to a recording device, a storage device, or a host processing system, or the like, as are known in the art. The apparatus may further comprise a transceiver functionality for sending and receiving data and/or signals from other sensors or external equipment such as a computer. In a manner similar to that illustrated in FIGS. 3 and 5, and the accompanying text, the microcontroller 92 is in communication with an antenna 96 on a top side of the third layer 62 by way of communication element 97 in the second intervening layer (layers 58/60, represented here as a single layer 59 for simplicity of illustration). A battery 98 disposed on the top side of the third layer 62 provides power to the sensors, microcontroller, antenna and transceiver. Optionally, the apparatus may include a power converter 100 that may receive power harnessed from radio waves (relayed by the antenna 96) to provide meet the power needs of the sensors, microcontroller, antenna and transceiver. Additionally, if the battery 98 is a rechargeable battery, the power converter 100 may continually recharge the battery.

Figure 10:
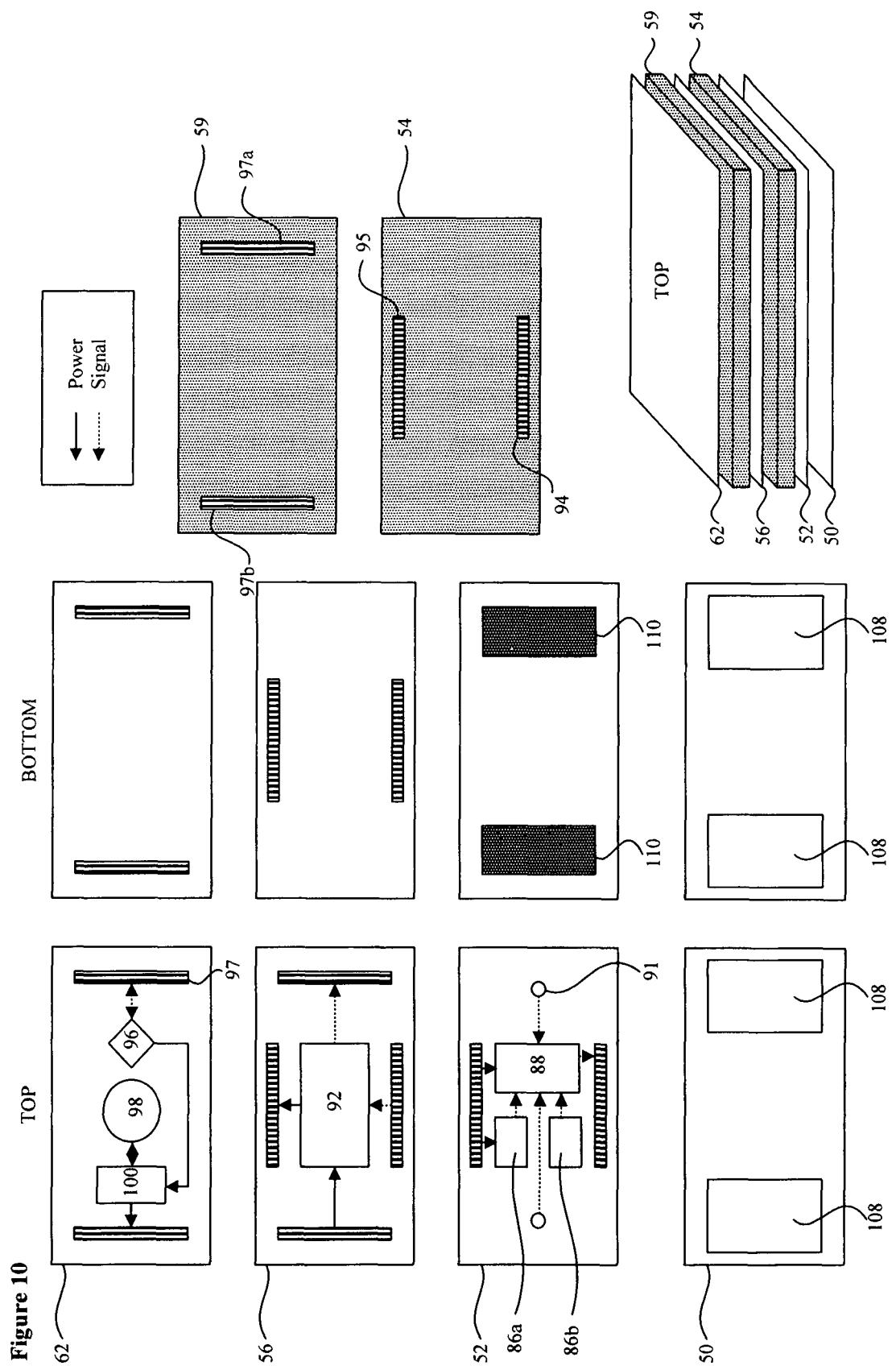
FIG. 10 shows an exploded view of an apparatus according to one embodiment of the invention, comprising a biopotential sensor and a motion sensor in the form of an accelerometer.

FIG. 10 shows an exploded view of an alternate embodiment of the invention combining an accelerometer and biopotential sensors in a single apparatus. Similar to the apparatus illustrated in FIG. 3, each of the first, second and third layers have a first ("top") and second ("bottom") side, and are configured to communicate with the adhesive layer, intervening layer, or both layers, on either side, to allow integration of the multiple sensors and components of the apparatus. The adhesive layer 50 has regions of conductivity 108 to allow electrical communication of a sensor 110 on the bottom of the first layer with the subject's skin surface. The sensor 110 may comprise an electrode. The sensor 110 is in communication with the signal conditioning module 88 on the top side of the layer 52 by way of communication element 91. Accelerometers 86a, 86b on a top side of the first layer 52 relays a signal to a signal conditioning module 88, for example using microcircuitry or fiber optics or the like (not shown), to provide data on positional change. The signal conditioning module 88 is in communication with a microcontroller 92 on a top side of the second layer 56 by way of a communication element 94, 95 in the intervening layer 54. The microcontroller 92 digitizes and processes the signals, which may be communicated to a recording device, a storage device, or a host processing system, or the like, as are known in the art. The apparatus may further comprise a transceiver functionality for sending and receiving data, signals or both data and signals from other sensors or external equipment such as a computer. In a manner similar to that illustrated in FIG. 3 and described in the accompanying text, the microcontroller 92 is in communication with an antenna 96 on a top side of the third layer 62 by way of communication element 97a, 97b in the second intervening layer (layers 58/60, represented here as a single layer 59 for simplicity of illustration). A battery 98 disposed on the top side of the third layer 62 provides power to the sensors, microcontroller, antenna and transceiver. Optionally, the apparatus may include a power converter 100 that may receive power harnessed from radio waves (relayed by the antenna 96) to provide meet the power needs of the sensors, microcontroller, antenna and transceiver. Additionally, if the battery 98 is a rechargeable battery, the power converter 100 may continually recharge the battery.

Also optionally, the apparatus illustrated in FIGS. 3, 5 and 6 may comprise other sensor modules or devices in or on the first layer 52, second layer 56 (not shown).

By combining a plurality of sensors at a single locus in one apparatus having a plurality of layers, synchronization of data is possible. For example placing an accelerometer capable of recording movement in three dimensions with an ECG electrode and collecting and processing the resulting data signals in a simultaneous and synchronous manner, ventricular ejection efficiency may be observed in combination with the electrical impulses of the cardiac cycle. This may eliminate the need to correlate or correct for distal placements of the separate sensors, or manage the operation of independent equipment that may provide incompatible data formats, and prevent synchronous analysis of the data.

It will be apparent to those skilled in the art that other combinations of biological parameters may provide synergistic advantages. For example, optical sensors for pulse oximetry may be combined with a sensor for ECG or an accelerometer, to provide blood oxygenation data synchronized with cardiac cycle information. As detailed above, Table 1 provides an exemplary list of parameters and devices or methods to measure them. Synchronized acquisition of data for at least two biological parameters may allow for correlation of intermittent aberrant data points, and/or identification of new correlations. This may also provide additional information to assist in removing motion, optical, acoustic, electrical or other artifacts associated with the various detection methods. Also, the subject may be provided with the advantage of being mobile while the device is in use.

Apparatus according to some embodiments of the invention, such as those exemplified herein, and as will be apparent to those skilled in the relevant art upon consideration of the examples and description, may also be improvements upon, or replacements for conventional procedures, devices and diagnostics. For example, combining an optical sensor for use in pulse oximetry with an accelerometer may be an improvement on conventional pulse oximetry. In another example, combining an acoustic sensor with a biopotential sensor may provide an improvement over the separate use of, for example, a stethoscope and an electrocardiograph. In another example, tissue imaging (i.e. for cancer or skin condition study and diagnosis, involving an optical sensor) may be combined with an accelerometer to allow identification of motion artifacts caused by movement of the subject.

Applications in the field of cardiology may be of particular use. For example, studies of the motion of the heart (ballistocardiogram, electrocardiogram, acoustic studies employing a stethoscope, or the like), may provide mechanical information on fluid flow, congestion, ventricular output, or changes in any of these due to aberrant muscle activity, tissue fatigue, tissue damage, blood clots or otherwise compromised blood flow etc. As an example, simultaneous detection of heart motion, heart rate and body position, in a non-invasive and synchronous manner may be useful to monitor cardiac performance in a subject under physiological stress conditions, such as an athlete, soldier, astronaut, or the like, during the physiological stress conditions (i.e long distance running, combat stress, sleep deprivation, lack of gravity, etc). Such monitoring may also be particularly useful in subjects having, or suspected of having a cardiac disorder that is intermittent or stress-induced.

Apparatus according to some embodiments of the invention may also aid diagnosis and/or monitoring of medical conditions or disorders that comprise multifactorial symptomatology. An apparatus according to some embodiments of the invention may comprise several sensors selected or designed for particular diagnostic applications, and provided as a single, 'ready-to-use' apparatus. Examples of conditions or disorders with multifactorial symptomatology include, but are not limited to seizures, transient ischemic events, various forms of valvular heart disease (ie mitral stenosis, mitral regurgitation, aortic stenosis, aortic regurgitation, tricuspid stenosis, tricuspid regurgitation) or the like. Additional details on these and other examples of conditions or disorders may be found in, for example, *Current Medical Diagnosis & Treatment* 43$^{rd}$ edition. Tierney, McPhee, Papadakis editors. Lange Medical Books/McGraw Hill, 2004.

Monitoring this range of symptoms with one or a few apparatus, rather than the combination of sensors, wires, computers and other monitoring devices may be less stressful and provide a more clinically useful baseline by reducing patient anxiety.

The small size of the apparatus according to some embodiments of the invention may also be used for continuous or long-term monitoring of specific biological parameters. For example an apparatus comprising microneedles in the adhesive layer may provide for continuous sampling of blood components, in a synchronous manner with other biological parameters In another embodiment of the invention, at least two multilayer sensor apparatus may be placed at first and second sites on a subject, to monitor differences or variability in at least two biological parameters at each of the first and second sites. The resulting signal and data stream are processed as described by each apparatus. To provide synchronization between the two apparatus' signal and data stream, the communication modules of each apparatus may further comprise a transceiver and communicate with other apparatus and a data storage device.

The term 'subject' is used to refer generally to any human or non-human animal. The subject may be a patient, including a veterinary patient, or may be an experimental animal, including a transgenic animal. The subject may be an athlete, or an athletic or sporting animal. Alternately, the subject may be an industrially-important animal such as livestock. The animal may be a primate or other mammal including, but not limited to, a mouse, rat or other rodent, cat, dog, goat, sheep, cow, pig, horse or other animal.

Fabrication

Various rapid prototyping, microfabrication and manufacturing methods are known, and may be suitable for the production of structural and or functional components of the apparatus according to some embodiments of the invention. Methods that may be useful for fabrication for the circuitry, the individual layers, various components may include, but are not limited to, stereolithography, microinjection moulding, LIGA (lithographie galvanoformung abformung), microlamination, microthermoforming, micro-surface printing, microembossing, soft lithography, electro plating, chemical or autocatalytic plating or the like. These and other related methods and techniques will be known to those skilled in the relevant art, and are described in, for example *Fundamentals of Microfabrication: The Science of Miniaturization.* 2$^{nd}$ edition by M. Madoy. CRC Press, 2004, or *Fundamentals of bioMEMS and Medical Microdevices.* 2006 by S S. Saliterman (SPIE Press) herein incorporated by reference. Communication elements or systems of communication elements, such as microfluidics systems for conveying reagents or analytes to or from a subject's skin, or between components of a system, or conductive wires may be microfabricated, using known methods. One method may be preferable over another for the fabrication of a particular sensor, component or other aspect of the system, and selection of a method of fabrication will be within the ability of an individual skilled in the relevant art.

Microintegration technologies may be adapted and applied to incorporate various sensors, data storage and communication aspects and the like in a single apparatus. Examples of such technologies are known in the art. In some embodiments, some communication elements, windows or apertures, etc, may be made an integral part of the layer or layers, while other components may be affixed to a sensor layer separately from the microfabrication step (ie by cold soldering, use of an adhesive, metallization or similar techniques) and connected to the communication elements or other components on the fabricated layer by conventional techniques (ie by cold soldering, use of an adhesive, metallization or similar techniques)

Encapsulation

Encapsulation of the apparatus in a polymer may provide physical and environmental protection, and/or insulation, for the various components of the apparatus. An encapsulant or encapsulating layer is generally an elastomeric or thermoplastic polymer, and may have varying degrees of rigidity or flexibility. The flexibility or rigidity of the encapsulate may be dependent on the nature of the sensor and/or the intended use of the apparatus. Alternately, a support substrate that exhibits elastomeric properties in only one dimension (ie longitudinally) may be used to provide the desired rigidity. The encapsulant may be opaque or transparent. In some embodiments, the encapsulate may be cast or shaped after casting. Encapsulates may comprise a variety of materials, including but not limited to silicone, rubber, polyimide SU8 negative epoxy resist, polymethyl methacrylate (PMMA), polycarbonate (PC). Additionally, the encapsulant may be photopatternable. The encapsulant may surround the apparatus on all sides, or may leave a portion of a side of the sensor uncovered, for example, to permit unobstructed contact of a subject's skin with the apparatus, or adhesive on the apparatus. For example, the encapsulant may cover the edges or ends, and a side of the apparatus that is opposed to the side configured for contact with a subject's skin or tissue, or an adhesive layer,

EXAMPLE METHODS

Fabrication of Test Apparatus

Fabrication and assembly of the test apparatus may be divided into three stages—fabrication of the polyimide circuit, device component population and encapsulation.

Printing of flexible circuit boards is known in the art (see, for example Printed Circuits Handbook 6$^{th}$ edition. C F Coombs, editor. McGraw-Hill 2007). Fabrication of the single-layer double-sided polyimide circuit was performed using a metal-on-polyimide rapid prototyping process, as is known in the art.

Components selected for use in the test apparatus were surface mount devices with a maximum size of 5×5×5 mm and a bonding pad pitch of at least 0.65 mm. A 3-axis MEMS interial sensor (LIS3L02AL—ST Microelectronics), and a conventional microcontroller were manually attached by cold soldering (silver epoxy and conductive ink).

Encapsulation

Populated test apparatus were encapsulated with silicone elastomer casting, using an electrical grade self-leveling silicone elastomer (Sylgard 184, Dow Corning). The populated test sensors were cleaned to remove oil or particulates, trimmed and placed in a mold of suitable size. The silicone encapsulant was prepared, degassed and poured over the test sensor in the mold, and heat cured, all according to manufacturer's instructions.

Test apparatus that were fabricated, populated and encapsulated as described were evaluated for flexibility and electrical insulation properties relative to the depth of the silicone encapsulate. An apparatus with a 5 mm encapsulate retained sufficient flexibility to bend about 30 degrees without visible cracking separation between the sensor substrate and encapsulant. An apparatus with an 0.5 mm encapsulate was sufficiently flexible to bend about 90 degrees, or wrap around a cylinder of approximate finger diameter, without visible cracking or separation between the apparatus substrate and encapsulant. A 0.5 mm silicone encapsulant was used.

The finished test apparatus used in the following non-limiting examples had dimensions of about 2×2.5 cm, and were about 0.5 mm thick. A 'flexible' apparatus was produced using a flexible polyimide support, while a 'rigid' apparatus was produced using an FR4 laminate circuit board support.

Example 1

Comparison of Multisensor With Conventional Accelerometer

Figure 7:
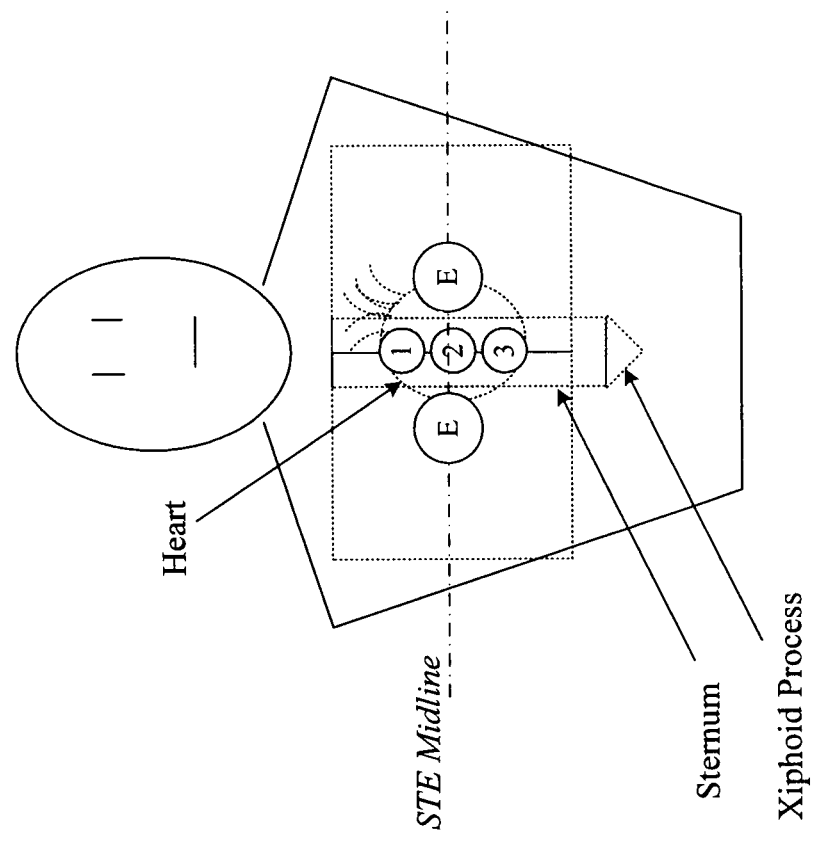
FIG. 7 shows sensor placement locations on a test subject. E—electrode location; numbers 1, 2, 3 denote sensor locations, in accordance with an embodiment of the invention.

FIG. 7 shows the sensor locations and reference electrode locations. Sensors were placed in three locations (1, 2, 3) along the subject's sternum for recording heart motion. A reference accelerometer (Bruel&Kjaer) was positioned at location 3. Rigid or flexible apparatus, each having identical components, were rotated between location 1 and location 2. Two electrodes were positioned about 2 inches apart, adjacent to the sternum along a sternal midline, to provide a reference ECG. Apparatus and ECG electrodes and leads were attached to the subject's skin surface with a conventional medical adhesive.

A total of four recordings (trials) were taken from the subject. Synchronized data samples were taken for a duration of 30-seconds at 500 Hz (each channel), for each of the four devices (2 test apparatus, one reference accelerometer and the reference ECG). Output from the sensors was conditioned (filtered and amplified) and conveyed to a data acquisition system (National Instruments NI 9205 DAQ).

Reference electrodes were connected to a conventional ECG (Burdick) with the analog output connected to the data acquisition system in the same manner as the sensors.

Figure 9:
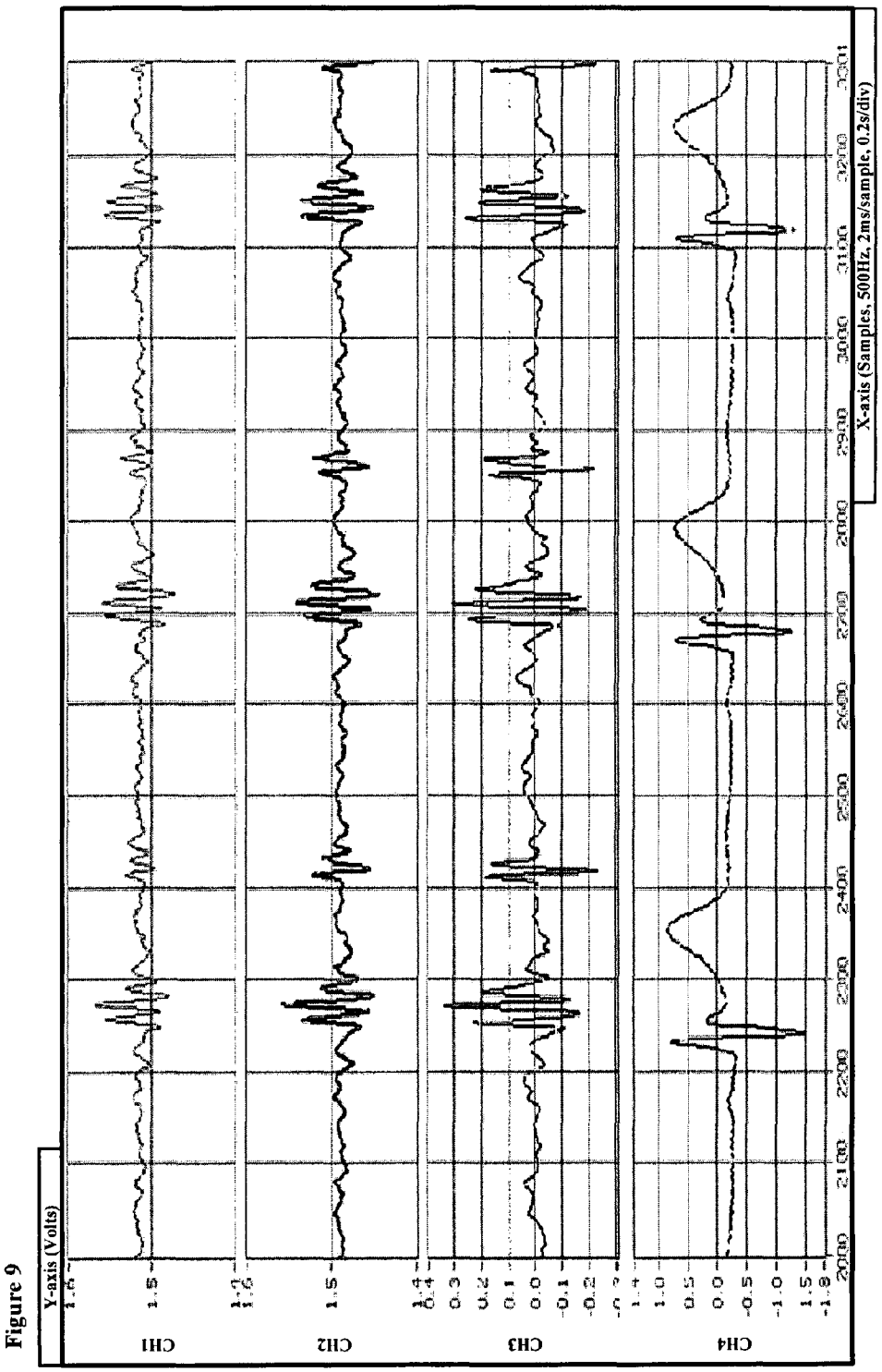
FIG. 9 shows an example of the recorded signals from trial I spanning approximately three heart-beats. Channel 1 (CH1)—signal recorded from the rigid sensor; channel 2 (CH2)—signal recorded from the flexible multisensor; channel 3 (CH3)—reference BCG signal; channel 4 (CH4)—reference ECG signal, in accordance with an embodiment of the invention.

FIG. 9 shows a portion of the recorded signals from trial I. The rigid (CH1) and flexible (CH2) signals were compared to the conventional accelerometer (CH3) and ECG (CH4) signals. The rigid and flexible sensors comprising MEMS accelerometers demonstrated a similar signal profile to that of the BCG reference signal (CH3).

Figure 8:
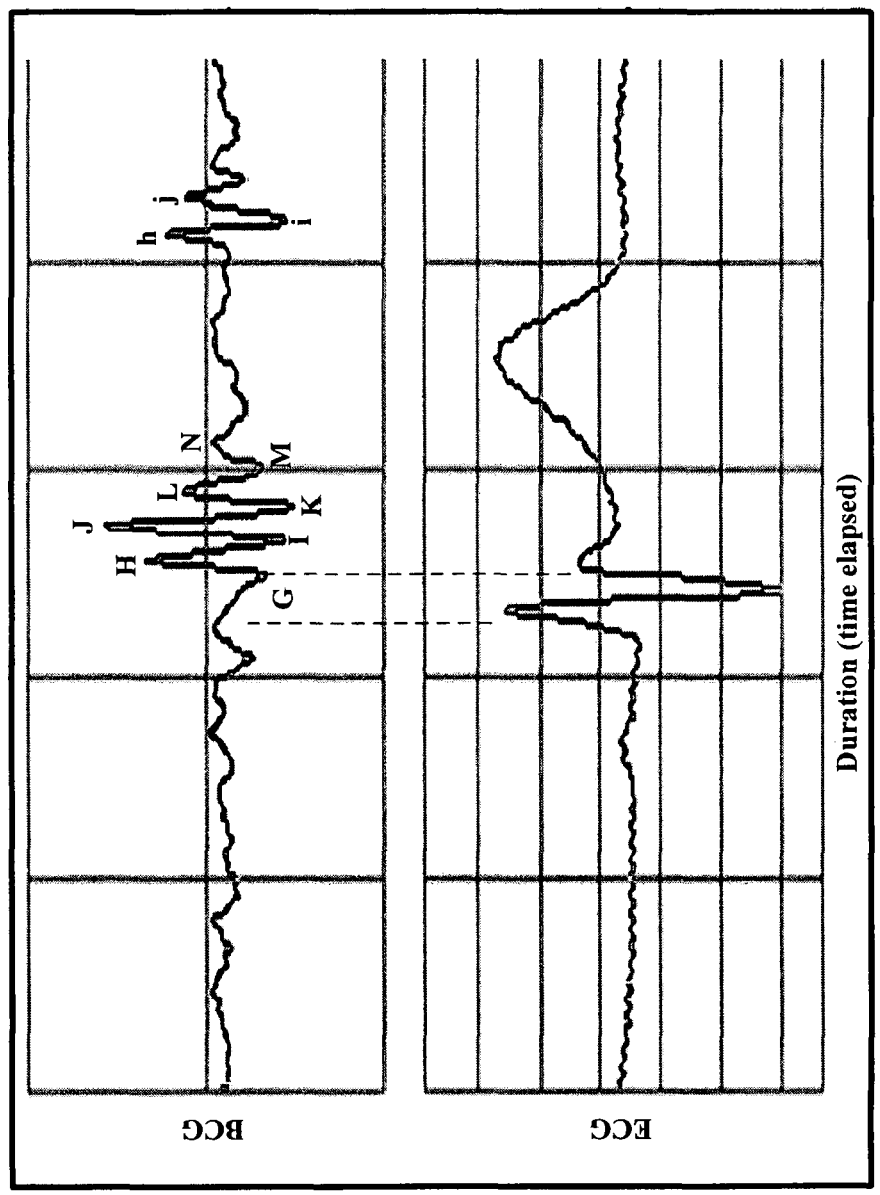
FIG. 8 shows a ballistocardiography signal of a single heart-cycle as recorded through the acquisition system of the flexible multisensor with reference to synchronized ECG, in accordance with an embodiment of the invention.

The resulting BCG signal demonstrates the expected components, as would be obtained using a conventional accelerometer for ballistocardiography, as described by McKay 1999 (Clin. Invest. Med 22:4-14), referenced to an ECG tracing. The aspects of the BCG wave (G, H, I, J, K, L, M and N waves) are visible and distinct (FIG. 8).

Table 2 summarizes the recordings at the sensor placements during the trial. From the combination of trials recorded and reference sensor comparison, the quality of signal related to sensor placement, and filtering differences can be qualitatively assessed.

TABLE 2

Summary of sensor recordings.

| Trial | Sensor | Location | Filter | Overall Sensitivity/Gain (approx.) |
|---|---|---|---|---|
| I | Rigid | 1 | 50 Hz | 3.0 V/g |
|  | Flex | 2 | 100 Hz | 3.0 V/g |
|  | Reference | 3 | 100 Hz | 9.8 V/g |
| II | Rigid | 2 | 50 Hz | 3.0 V/g |
|  | Flex | 1 | 100 Hz | 3.0 V/g |
|  | Reference | 3 | 100 Hz | 9.8 V/g |
| III | Rigid | 1 | 100 Hz | 3.0 V/g |
|  | Flex | 2 | 50 Hz | 3.0 V/g |
|  | Reference | 3 | 100 Hz | 9.8 V/g |

TABLE 2-continued

Summary of sensor recordings.

| Trial | Sensor | Location | Filter | Overall Sensitivity/Gain (approx.) |
|---|---|---|---|---|
| IV | Rigid | 2 | 100 Hz | 3.0 V/g |
| | Flex | 1 | 50 Hz | 3.0 V/g |
| | Reference | 3 | 100 Hz | 9.8 V/g |

Figure 12:
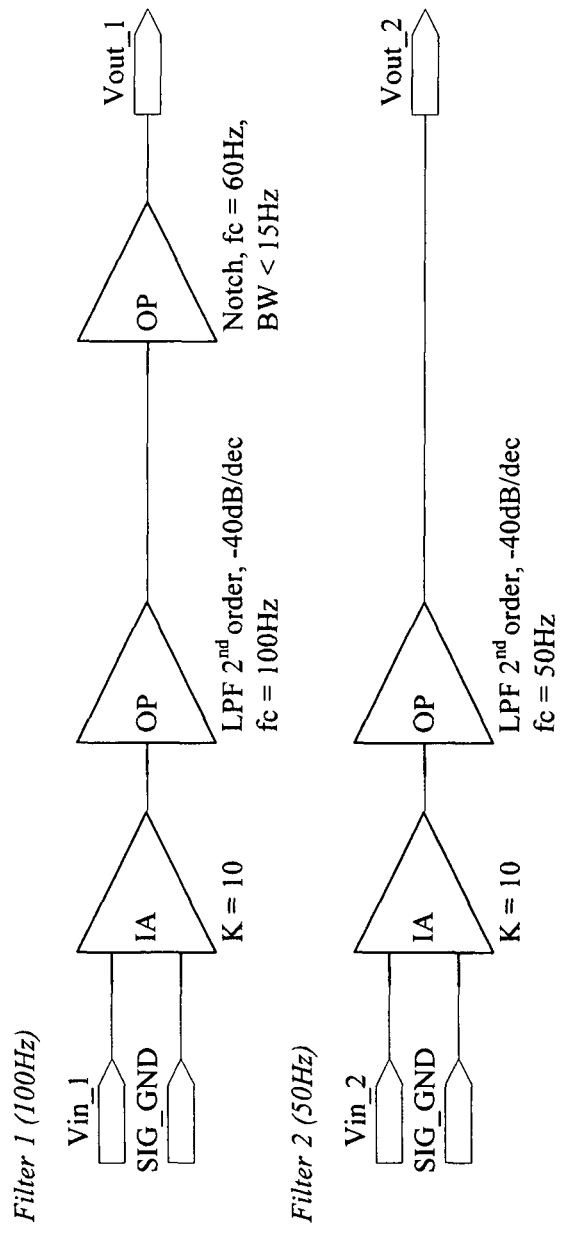
FIG. 12 shows a gain-map for two signal conditioning modules 50 Hz and 100 Hz, illustrating generally the steps followed in the signal conditioning process, in accordance with an embodiment of the invention.

Results from trials I and III demonstrated that altering the filtering cut-off frequencies at the signal conditioning stage did not affect the signal. A low-pass filter was used, as indicated in Table 2. A schematic (FIG. 12) illustrates generally the steps followed in the signal conditioning process.

Apparatus type (rigid vs flexible) had little to no effect on signal morphology, however positional effects of the sensors (at location 1 or 2) did affect signal morphology.

All citations are herein incorporated by reference.

One or more exemplary embodiments have been described by way of example. It will be apparent to persons skilled in the art that a number of variations and modifications can be made without departing from the scope of the invention as defined in the claims.

What is claimed is:

1. An apparatus configured to monitor one or more than one biological parameter, the apparatus comprising:
the following components:
(a) a first sensor, wherein the first sensor is an accelerometer;
(b) one or more second sensors for sensing one or more than one biological parameter;
(c) a signal conditioning module in communication with one or more than one of the first and second sensors;
(d) a signal processor in communication with the signal conditioning module and producing a processed signal;
(e) a communication module in communication with the signal processor and transmitting the processed signal to a storage module, a display device, a host processing system, or a combination thereof; and
(f) a power module to provide power to the first and second sensors, the signal conditioning module, the signal processor, and the communication module; and
a first layer comprising a first flexible substrate and one or more of the components;
a second layer comprising a second flexible substrate and one or more of the components; and
an intervening layer comprising a third flexible substrate and one or more communication elements configured to permit communication between one or more components of the first layer and one or more components of the second layer;
wherein the third flexible substrate is positioned between the first flexible substrate and the second flexible substrate.

2. The apparatus of claim 1 wherein the signal processor comprises the signal conditioning module.

3. The apparatus of claim 1 further comprising an adhesive layer.

4. The apparatus of claim 1 wherein the one or more than one biological parameters are independently selected from the group comprising: movement, heart rate, motion associated with the cardiac cycle, ventricular output, ventricular ejection efficiency, temperature, biopotential, respiration, skin moisture, skin conductivity, hemoglobin oxygen saturation, sound, light absorption or reflection, glucose level, protein level, amino acid level, lipid level, fatty acid level and a combination thereof.

5. The apparatus of claim 1 wherein the second sensor is a biopotential sensor.

6. The apparatus of claim 1 wherein the second sensor is a spectrometer.

7. The apparatus of claim 1 wherein the second sensor comprises electrodes for obtaining an electrocardiogram.

8. The apparatus of claim 1 wherein the first flexible substrate and the second flexible substrate comprise polyimide.

9. The apparatus of claim 1 wherein the power module comprises a battery, a radiofrequency power source, a piezoelectric crystal, a thermocouple, or a combination thereof.

10. The apparatus of claim 1, comprising three sensors.

11. The apparatus of claim 1 wherein the second sensor is independently selected from the group consisting of: accelerometer, electrode, thermometer, thermal diode, galvanometer, LED, photodiode, microphone, vibration sensor, optical diode, glucometer, spectrometer, pH meter, spectrophotometer, acoustic sensor, biopotential sensor, and a combination thereof.

12. The apparatus of claim 1 wherein the second sensor is an acoustic sensor.

13. The apparatus of claim 1 wherein the second sensor is a biopotential sensor.

14. A method for monitoring one or more than one biological parameter, the method comprising:
(a) positioning the apparatus of claim 1 on a subject;
(b) obtaining and monitoring a first processed signal from the accelerometer with the apparatus;
(c) obtaining and monitoring a second processed signal from the second sensor;
thereby monitoring a movement of at least a portion of the subject simultaneously and synchronously with monitoring the signal of the second sensor to monitor an alteration in one or more than one biological parameters.

15. The apparatus of claim 1, wherein the intervening layer is an electrically insulating layer.

16. The apparatus of claim 1, wherein the accelerometer is a 3-axis accelerometer.

17. The apparatus of claim 7, wherein the one or more than one biological parameters are parameters associated with the cardiac cycle.

18. The method of claim 14, wherein the accelerometer is a 3-axis accelerometer.

19. The method of claim 14, wherein the movement of at least a portion of the subject is movement associated with the cardiac cycle and the first processed signal comprises ballistocardiograph data.

20. The method of claim 19, wherein the second sensor comprises electrodes and the second processed signal comprises electrocardiograph data.

21. The method of claim 14, wherein the apparatus is positioned on the subject at a first site and wherein the method further comprises positioning a second apparatus according to claim 1 on the subject at a second site.

* * * * *